United States Patent [19]

Cerf et al.

[11] Patent Number: 5,064,294
[45] Date of Patent: Nov. 12, 1991

[54] PROCESS AND APPARATUS FOR INVESTIGATING AND CONTROLLING CHANGES OF STATE OF A LIQUID OR GELLED MEDIUM BY DIFFERENTIAL THERMAL ANALYSIS

[75] Inventors: Olivier Cerf, Paris; Jean-Pierre Pain, Le Meux; Gérard Antonini, Paris, all of France

[73] Assignee: Institut National de la Recherche Agronomique, Paris, France

[21] Appl. No.: 543,789
[22] PCT Filed: Jan. 25, 1989
[86] PCT No.: PCT/FR89/00022
  § 371 Date: Sep. 18, 1990
  § 102(e) Date: Sep. 18, 1990
[87] PCT Pub. No.: WO89/06794
  PCT Pub. Date: Jul. 27, 1989

[30] Foreign Application Priority Data

Jan. 25, 1988 [FR] France .................... 88/00803

[51] Int. Cl.$^5$ .............................. G01N 25/04
[52] U.S. Cl. ........................ 374/16; 374/25; 436/147
[58] Field of Search ............ 374/16, 21, 25, 10, 374/11; 422/109; 436/147; 73/64.1

[56] References Cited

U.S. PATENT DOCUMENTS

| | | | |
|---|---|---|---|
| 2,922,304 | 1/1960 | Lees et al. | 374/25 |
| 3,643,491 | 2/1972 | Dell et al. | 374/11 |
| 3,675,465 | 7/1972 | Sommer et al. | 374/11 |
| 4,040,288 | 8/1977 | Kotelnikov et al. | 374/11 |
| 4,255,962 | 3/1981 | Ashman | 374/10 |
| 4,567,849 | 2/1986 | Wan | 374/11 |
| 4,601,587 | 7/1986 | Mathiprakasam | 374/16 |
| 4,611,928 | 9/1986 | Hori et al. | 374/21 |
| 4,663,169 | 5/1987 | Hori et al. | 374/16 |
| 4,783,174 | 11/1988 | Gmelin et al. | 374/11 |
| 4,812,051 | 3/1989 | Paulik et al. | 374/10 |
| 4,967,593 | 7/1989 | McQueen | 374/10 |
| 4,971,451 | 11/1990 | Hori et al. | 374/25 |
| 4,981,369 | 1/1991 | Kumada et al. | 374/16 |

FOREIGN PATENT DOCUMENTS

| | | | |
|---|---|---|---|
| 0100039 | 6/1985 | Japan | 374/16 |
| 0200230 | 7/1967 | U.S.S.R. | 374/16 |
| 0325548 | 1/1972 | U.S.S.R. | 374/10 |
| 8707716 | 12/1987 | World Int. Prop. O. | 374/25 |

OTHER PUBLICATIONS

White, J. L. et al., "Application of Differential Thermal Colorimetry to Measurements of Stored-Energy Release in Metals", Rev. Scientific Instrum., vol. 34, No. 10, (Oct. 1963).
"Soviet Inventions Illustrated", Week E19, No. 6456 E/19 * SU 851222, 6/23/82.

Primary Examiner—William A. Cuchlinski, Jr.
Assistant Examiner—Diego F. F. Gutierrez
Attorney, Agent, or Firm—Berman & Aisenberg

[57] ABSTRACT

Gelling of a liquid or liquefication of a gel are investigated or controlled by differential measurement of thermal characteristics of the involved medium. The temperature of the medium is measured by a first probe (delivering a first temperature indicating signal) while a second probe (sufficiently far away from the first probe not to disturb the latter through temperature changes) imparts heat to said medium and delivers a signal corresponding to its temperature. The signals respectively emitted by the probes are processed in an electrical data processing unit wherein the signals are combined in a correcting stage which corrects the signal delivered by the second probe taking into account the signal delivered by the first probe to deliver information indicating the change of state of the medium.

10 Claims, 3 Drawing Sheets

PROCESS AND APPARATUS FOR INVESTIGATING AND CONTROLLING CHANGES OF STATE OF A LIQUID OR GELLED MEDIUM BY DIFFERENTIAL THERMAL ANALYSIS

FIELD OF THE INVENTION

The present invention relates to a process for investigating and controlling changes of state of a liquid or gelled medium—for example of the gelling of a liquid fluid or the liquefaction of a gel, by differential measurement of thermal characteristics of the involved medium.

The invention is also aimed at a device for making use of this process. This invention applies more particularly to food industries.

BACKGROUND

A process for the application of the hot wire anemometry principle to follow milk coagulation is described in document EP-A-0-144,443. This method makes it possible more generally to follow a liquid-gel transition under isothermal conditions. In fact, energy is introduced into initially liquid medium in the form of heat by means of a platinum wire, after which a measurement of the temperature of this wire is carried out. In a liquid medium, natural convection produces an equilibrium of heat transfers between the wire and the product so that the wire temperature is constant, slightly higher than that of the surrounding medium. If the medium coagulates or gels, the change in the structure of this medium is accompanied by a change in the thermal regime with a changeover from natural convection to conduction. This is reflected in an increase in the temperature of the platinum wire, which corresponds to a change in the heat transfer coefficient in the medium, since the heat conductivity of the latter remains constant. In the food industry field, firstly, the isothermal state is never perfectly achieved and, secondly, many cases of gelling or of coagulation are coupled with a temperature change, for example the gelling of gelatin, of polysaccharides and, more generally, the manufacture of sauces and of jams, as also is the coagulation on heating of milk to which rennet has been added when cold, etc. In the cases set out above the perturbations introduced by the temperature change do not allow the sensor proposed in the abovementioned patent to display the coagulation phenomenon.

SUMMARY OF THE INVENTION

An object of the present invention is to take into account temperature changes in the medium which is capable of being coagulated or gelled in order to control and to investigate the changes of state of this medium.

Another object of the present invention is to employ these characteristics to obtain information relating solely to the coagulation phenomena in the strict meaning of the term.

The subject of the present invention is therefore a process for investigating and controlling the phenomena of gelling of a liquid fluid or of liquefaction of a gel by differential measurement of the thermal characteristics of the said medium, characterized in that the measurement of the temperature of the medium is carried out by means of a first probe delivering a first signal indicating the temperature of this medium, while contributing energy in the form of heat to the said medium by means of a second probe which is sufficiently far away from the first probe not to disturb the latter through the temperature changes, this second probe delivering a signal corresponding to its temperature, after which the signals emitted by the probes are processed, after amplification and correction, in an electrical data processing unit, using the medium temperature measurement signal to correct the signal supplied by the second heat quantity probe, so as to make the data contained in the signal relate to the coagulation phenomena in the strict meaning of the term.

The invention also extends to a device for sensing the thermal characteristics of a liquid fluid in the course of gelling, more particularly intended for making use of the abovementioned process, this device being characterized by the coupling of a first probe ensuring the measurement of the temperature of the liquid fluid and of a second probe intended to contribute energy in the form of heat to the medium, these two probes delivering signals which are transferred, after amplification and correction, to an electrical data processing unit.

According to the present invention platinum resistance probes are advantageously employed.

Other advantages and characteristics of the present invention will become apparent on reading the forms and examples of embodiment which are described in what follows with reference to the attached drawings, in which:

DETAILS

Figure 1:
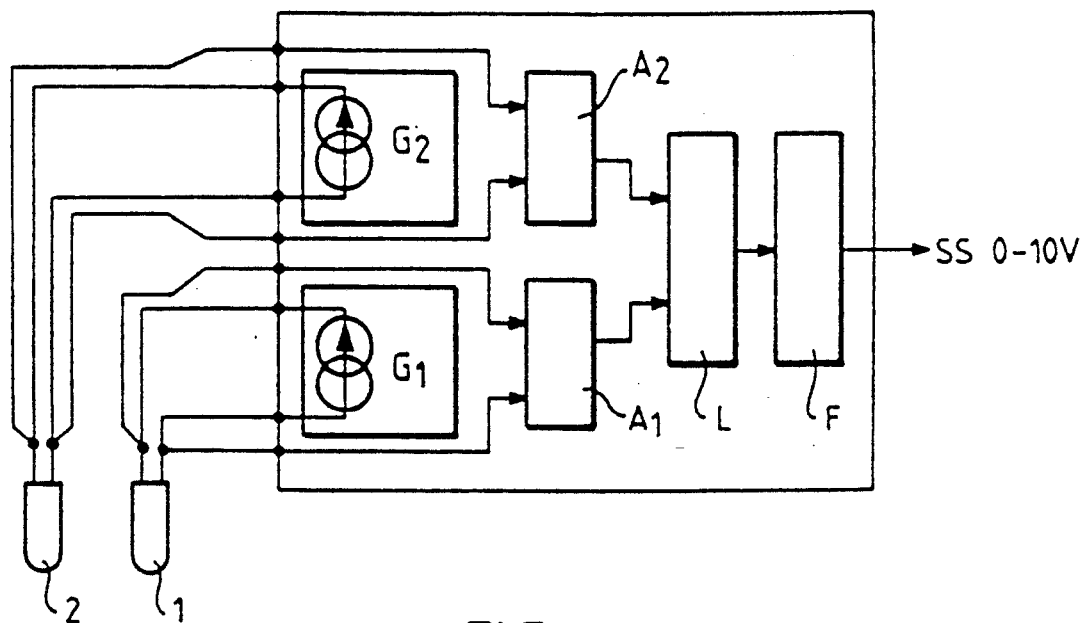
FIG. 1 is a diagrammatic view of the sensor device according to the present invention.

The sensor device shown in FIG. 1 comprises two 100-ohm (at 0° C.) platinum resistance probes 1, 2 packaged in a glass ampule, exhibiting, for example, a diameter of 2 mm for a length of 12 mm. The first probe 1, called a temperature probe, ensures the measurement of the temperature of the medium, while the second probe 2, called a heat quantity probe, contributes energy in the form of heat to the medium and delivers a signal which shows its own temperature. The dimensions of the heat quantity probe 2 are chosen as a function of the product being investigated in order to conform to a quantity of heat supplied per unit surface area which is sufficiently low to endow the sensor with a quality of fineness or discreteness. Such probes can be readily obtained commercially.

A platinum probe packaged in this way provides a mobility and especially a higher sensitivity than the temperature sensors of the thermocouple type which are generally employed. The compromise between fineness and sensitivity is produced by packaging of the heating platinum probe described above.

Heating of the platinum wire of the heat quantity probe 2 is ensured by a Joule effect from a calibrated source of current $G_2$ of a constant intensity, for example of 35 mA, which gives a power of 0.2 watts for a flux density equal to 1600 W/m². This current must be sufficiently stable and, moreover, independent of any resistance change to allow this resistance to be measured. Thus, the current sources employed $G_1$ and $G_2$ employing a high-gain amplifier and an FET-MOS transistor with excellent voltage insulation, ensure a current stability of 0.1 mA for a 10% change in the load resistance. The signal originating from the heat quantity probe 2 is then amplified in stage $A_2$ before being combined, in analog or digital fashion, in a correcting stage L with the signal originating from the temperature probe 1. The correcting stage L corrects the signal emitted by the probe 2 taking into account the signal emitted by the probe 1 to deliver information which indicates strictly the state of change of the medium.

The measurement of the temperature of the heat quantity probe 2 corresponds to the measurement of change in the resistance of the platinum wire which is known from the change in the voltage at the terminals of this wire. Thus, in the case of a constant current I, this gives:

$V_2(T) = R_2(T) \times I_2$, T being the temperature of the probe 2. Before any change in the structure of the product, the heat quantity probe delivers a non-zero signal $V_o$, which is a function of the product temperature $\theta$. In an isothermal state, when $\theta$ is constant, $V_o$ is a constant and only the difference $V_2(T) - V_o$ is significant of change in structure. $V_0$ is then considered as an offset voltage which is written $V_d$.

When the change in structure of the product being investigated is a corollary of a temperature change, the offset voltage $V_d$ is no longer constant but is a function of the product temperature $\theta$. The temperature probe 1 which is supplied by the generator $G_1$ with a current of 1 mA intensity delivers an analog voltage $V_1(\theta)$ proportional to the temperature $\theta$. After suitable calibration, the offset voltage to be deducted from the signal supplied by the heat quantity probe 2 can be calculated at the L stage, after amplification in $A_2$ either by an analog method with an electronic adder, or by a digital method with a microcomputer or the like. For example, with a calibration in water between 10° and 80° C., using a signal gating chart endowed with an electronic adder, the offset voltage $V_d(T)$ can be related to $V_1(\theta)$ by an equation of the type $aX+b$. The signal V (T) delivered by the heat quantity probe 2, reduced by the offset voltage $V_d(T)$ is then amplified in the F stage.

The sensitivity of a platinum resistance probe is in the neighbourhood of 0.4 (lacuna)/°C. With I $(G_2) = 35$ mA, a sensitivity of 14 mV/°C. is obtained. The sensitivity of a thermocouple is 40 μV/°C.

Thus, when compared with a sensor of the thermocouple type, the ratio of the sensitivities is 350 in favour of the platinum resistance probe, with the result that the circuit with the platinum resistance probe ensures, with a single amplification stage F with a gain of 100, a relatively noiseless and highly sensitive signal. In addition, a single low-pass filter with a cutoff frequency below 1 Hz is sufficient.

The following examples of application are given purely by way of illustration and do not in any way limit the scope of the present invention.

EXAMPLE 1—Gelling

The work is done on three solutions of gelatin.

Figure 2:
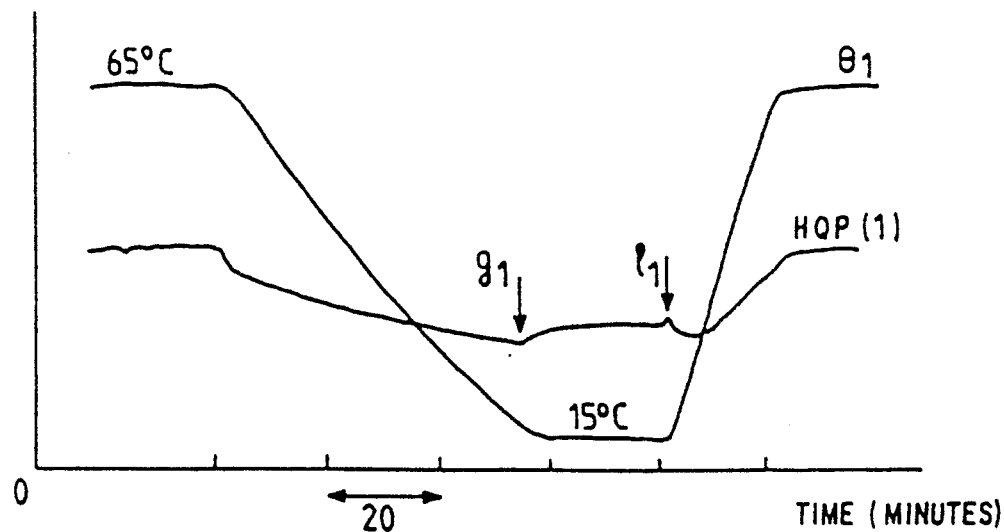
FIG. 2 shows the $\theta_1$ (temperature probe) and HQP (1) (heat quantity probe) curves illustrating the gelling kinetics of a solution of gelatin at a concentration of 1%.
Figure 3:
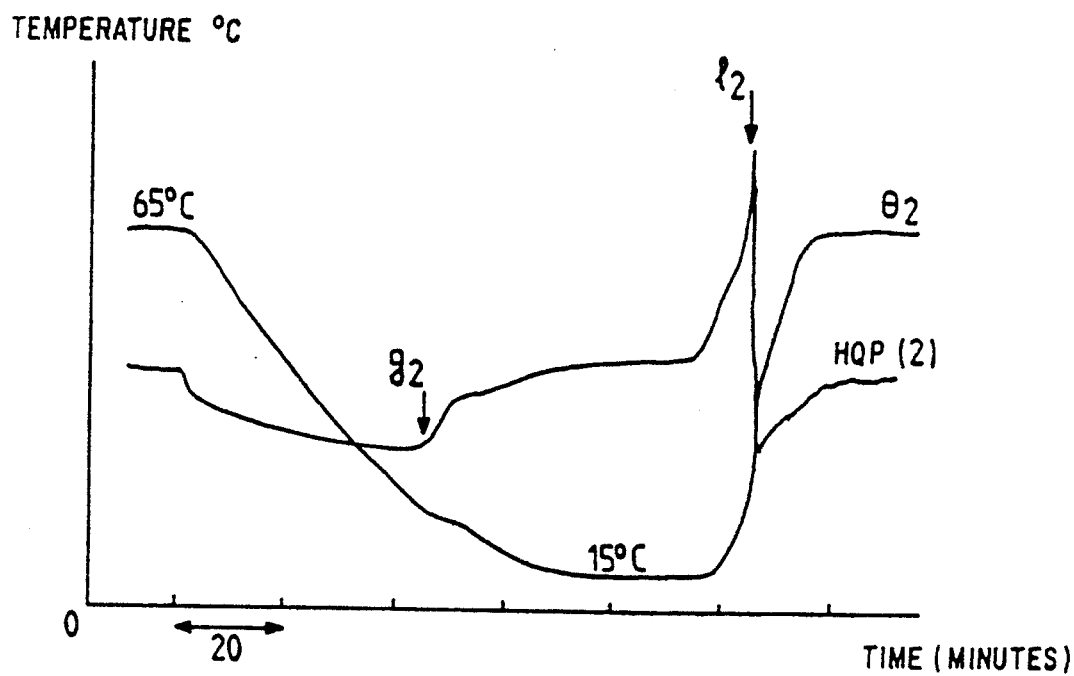
FIG. 3 shows the $\theta_2$ (temperature probe) and HQP (2) (heat quantity probe) curves illustrating the gelling kinetics of a solution of gelatin at a concentration of 5%.
Figure 4:
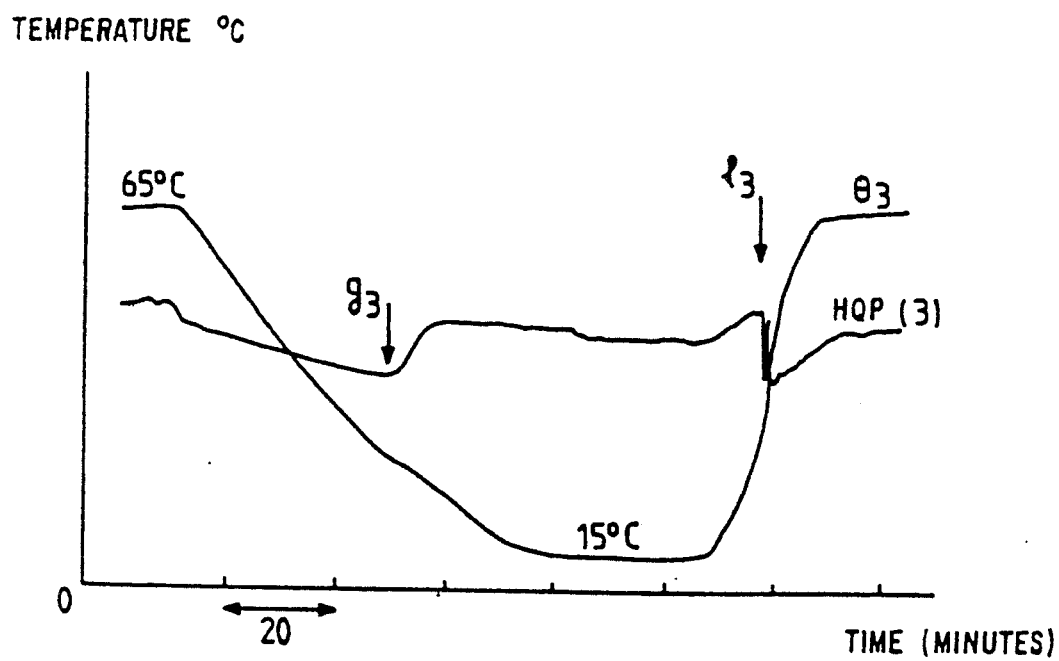
FIG. 4 shows the $\theta_3$ (temperature probe) and HQP (3) (heat quantity probe) curves illustrating the gelling kinetics of a solution of gelatin at a concentration of 10%.

A specified quantity of gelatin powder has been dissolved in distilled water and then heated in a microwave oven until completely dissolved. The solution obtained is divided into two beakers, each of 50 ml. The latter are placed in a water bath, the temperature probe is immersed in the first beaker, the heat quantity probe in a second beaker. In this way the heat quantity probe does not perturb the measurement of the temperature of the medium. The signals delivered by the two probes are recorded continuously. FIGS. 2, 3 and 4 show the results obtained with solutions of gelatin at three different concentrations, 1%, 5% and 10% respectively. These solutions are subjected to a temperature decrease from 65° C. to 15° C., followed by an increase by the same amount.

While the temperature is decreasing, a slight drift of the signal delivered by the heat quantity probe is noted, a drift due to the use of an analog method for calculating $V_d$. It should be noted that the use of a digital method would allow this drift to be eliminated. Then, when the gelling temperature is reached, at $g_1$, $g_2$, $g_3$ respectively, the slope of the signal reverses. The magnitude of this slope and the gelling temperature are a function of the concentration of gelatin in the solution. Lastly, while the temperature rises, a large increase in the signal appears, which can be associated with the phenomenon of gel liquefaction, for example at $l_1$, $l_2$ and $l_3$ respectively in FIGS. 2, 3 and 4, this phenomenon being the reverse of gelling.

EXAMPLE 2—Coagulation of a milk to which rennet has been added when cold

It is known that enzymatic hydrolysis takes place normally in a milk to which rennet has been added when cold. On the other hand, the formation of the protein network which constitutes the coagulation in the proper sense does not take place, the milk to which rennet has been added thus remaining liquid. It is possible, however, to obtain the formation of the protein network by increasing the temperature after a certain time of keeping cold. These phenomena have made it possible to develop a cheesemaking technology process, called the Stenne-Hutin process (1965).

Figure 5:
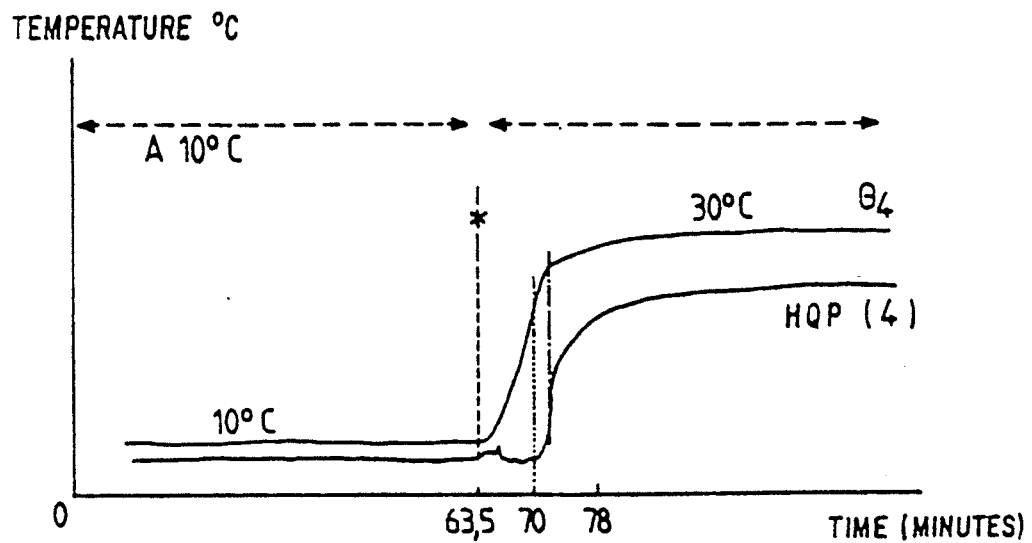
FIG. 5 shows the $\theta_4$ (temperature probe) and HQP (4) (heat quantity probe) curves illustrating the coagulation kinetics of a milk to which rennet has been added when cold.

The sensor device of the present invention makes it possible to follow the progress of the phenomena. In the example illustrated in FIG. 5 the milk employed is reconstituted from a skimmed milk powder in a proportion of 100 g/liter, to which 1 mmol/kg of $CaCl_2$ has been added, the pH of rennet addition being 6.63. The coagulating agent is then added in the form of a solution prepared from rennet powder, namely 50 mg/kg of milk, that is 222 μg/kg of active chymosin. A coagulation of this milk is normally obtained in 15 minutes at 30° C.

In the present case, the milk to which rennet has been added is kept at 10° C. for approximately 1 hour, after which it is subjected to a temperature increase from 10° to 30° C. by means of a water bath, which requires 8 minutes. Throughout the period when the milk to which rennet has been added is kept at 10° C. the heat quantity probe shows no signal change. When the temperature set point of the water bath is changed the signal oscillates in a disordered manner around a mean value close to the preceding value, thus reflecting the natural convection phenomena. When the temperature approaches 30° C. the signal of the heat quantity probe increases abruptly before reaching a plateau. It is then possible to associate the time of the visual detection of the formation of the network, that is to say the cheesemaker's setting time substantially at the time of the point of inflection of the curve.

Figure 6:
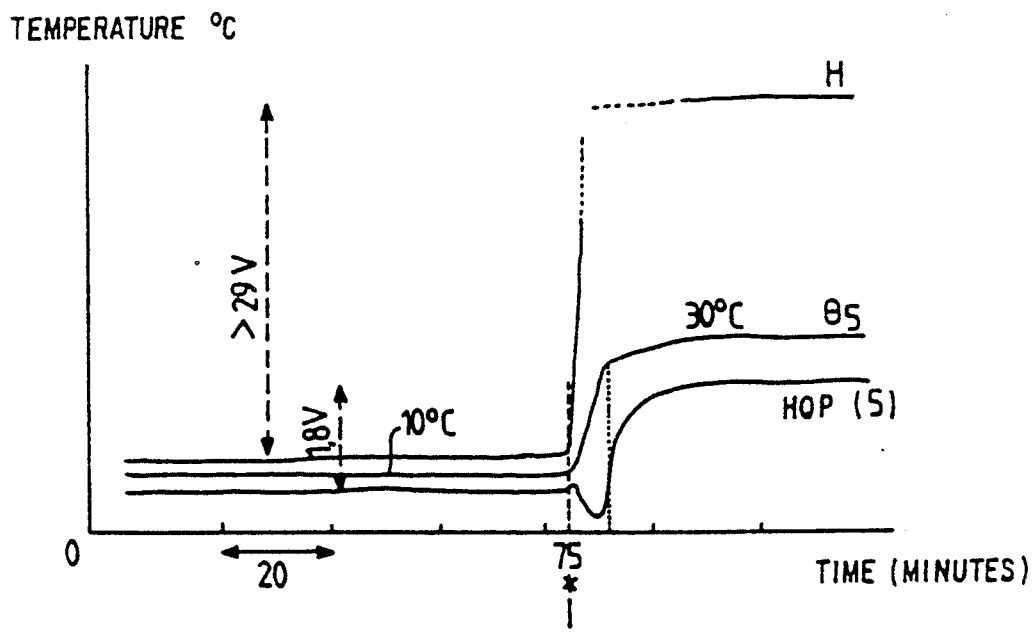
FIG. 6 shows the H, (Hori type probe), HQP (5) (heat quantity probe) and $\theta_5$ (temperature probe) curves illustrating the coagulation kinetics of another milk to which rennet has been added when cold.

FIG. 6 shows the same type of kinetics by comparing the results obtained in the curves $\theta_5$ and $HQP_5$ with the sensor device according to the invention and in the curve H obtained with a probe of the type described by Hori in EP-A 0,144,443. As soon as the temperature set point change begins, curve H shows that the signal of the Hori-type probe increases abruptly. It should be noted that this change, whose total amplitude is greater than 20 volts, does not allow the coagulation time to be detected, in contrast to the signal of the heat quantity probe incorporated in the sensor device of the present invention.

Thus, the problem of controlling the change and the coagulation of foodstuff products is found to be solved according to the present invention by virtue of the coupling of the two probes incorporated in the sensor device which makes it possible, in particular, to supply an output signal indicating any change in a medium which is reflected in a change in the heat transfer coefficient and consequently in convection within this medium.

It is clear that the present invention is not limited in any way to the forms and embodiments described above, but that it includes all the modifications and alternative versions within the reach of a specialist. Similarly, the references to the drawings are given merely by way of explanation and without limiting the present invention in any way. Furthermore, it should be stated that the reference signs inserted after the technical characteristics referred to in the claims are solely intended to facilitate understanding of the latter and do not limit their scope in any way.

We claim:

1. A process for investigating changes of state of a liquid or gelled medium by differential measurement of the thermal characteristics of the medium, the improvement comprising the following steps:
   measuring the temperature of the medium by means of a first probe (1) delivering a first signal indicating the temperature of this medium,
   contributing energy to the medium in the form of heat by means of a second probe (2) which delivers a signal indicating the temperature of this second probe (2),
   after amplification, combining the abovementioned signals in a correcting stage (L) which corrects the signal delivered by the second probe (2) taking into account the signal delivered by the first probe (1) to deliver information strictly indicating the change of state of the medium.

2. A process according to claim 1, characterized in that the signal delivered by the correcting stage (L) is amplified.

3. A process according to claim 1, characterized in that the correction in the stage (L) is carried out by employing an electronic adder.

4. A process according to claim 1, characterized in that the correction in the stage (L) is carried out digitally with the aid of a microcomputer.

5. A process according to claim 1, characterized in that the abovementioned probes (1, 2) are 100-ohm platinum resistance probes.

6. A process according to claim 1, characterized in that the probes (1, 2) are fed with a low current.

7. A process according to one of claims 1 to 6, characterized in that the second probe (2) is arranged sufficiently far away from the first probe (1) not to disturb the latter with respect of temperature.

8. A device for making use of the process of claim 1, which comprises a first probe (1) for measuring the temperature of the medium and delivering a corresponding signal, a second probe (2) for contributing energy to the medium in the form of heat and delivering a signal indicating its own temperature, means for amplifying (A1, A2) the signals and means for correcting (L) the signal delivered by the second probe (2) by means of the signal delivered by the first probe (1).

9. A device according to claim 8, characterized in that it additionally comprises means for amplifying (F) the signal delivered by the said correcting means (L).

10. A device according to either claims 8 or 9, characterized in that the probes (1, 2) are platinum resistance probes.

* * * * *

UNITED STATES PATENT AND TRADEMARK OFFICE
CERTIFICATE OF CORRECTION

PATENT NO. : 5,064,294

DATED : November 12, 1991

INVENTOR(S) : NOEL

It is certified that error appears in the above-identified patent and that said Letters Patent is hereby corrected as shown below:

Title Page, left column, Item [75] "Inventors:" should read --Inventors: Yolande Noel, Sucy-en-Brie; Jean-Luc Bellon, Antony; Jean-Marie Herry, Arpajon;--.

Signed and Sealed this

Second Day of March, 1993

*Attest:*

STEPHEN G. KUNIN

*Attesting Officer*  *Acting Commissioner of Patents and Trademarks*